(12) United States Patent
Reiderman et al.

(10) Patent No.: US 7,697,375 B2
(45) Date of Patent: Apr. 13, 2010

(54) COMBINED ELECTRO-MAGNETIC ACOUSTIC TRANSDUCER

(75) Inventors: Arcady Reiderman, Houston, TX (US); Joseph G. Barolak, Spring, TX (US)

(73) Assignee: Baker Hughes Incorporated, Houston, TX (US)

(*) Notice: Subject to any disclaimer, the term of this patent is extended or adjusted under 35 U.S.C. 154(b) by 504 days.

(21) Appl. No.: 11/748,165

(22) Filed: May 14, 2007

(65) Prior Publication Data

US 2007/0211572 A1  Sep. 13, 2007

Related U.S. Application Data

(63) Continuation-in-part of application No. 10/971,485, filed on Oct. 22, 2004, now Pat. No. 7,311,143.

(51) Int. Cl.
*G01V 1/40* (2006.01)
(52) U.S. Cl. .................. 367/168; 367/35; 73/642; 73/643
(58) Field of Classification Search ............ 367/31, 367/32, 35, 168; 73/642, 643
See application file for complete search history.

(56) References Cited

U.S. PATENT DOCUMENTS

| | | | | |
|---|---|---|---|---|
| 2,660,249 A | 11/1953 | Jakosky | ............ | 166/60 |
| 3,191,144 A | 6/1965 | Pardue | ............ | 367/25 |
| 3,221,548 A | 12/1965 | Wilson | ............ | 73/152.15 |
| 3,512,407 A | 5/1970 | Zill | ............ | 73/152.15 |
| 3,724,589 A | 4/1973 | Chapman, III | ............ | 367/30 |
| 4,218,924 A * | 8/1980 | Fortunko et al. | ............ | 73/642 |
| 4,248,092 A * | 2/1981 | Vasile et al. | ............ | 73/643 |
| 4,434,663 A | 3/1984 | Peterson et al. | ............ | 73/643 |
| 4,466,287 A * | 8/1984 | Repplinger et al. | ............ | 73/643 |
| 4,495,606 A | 1/1985 | Smith | | |
| 4,604,612 A * | 8/1986 | Watkins et al. | ............ | 367/168 |
| 4,805,156 A | 2/1989 | Attali et al. | ............ | 367/35 |
| 4,893,496 A | 1/1990 | Bau et al. | | |
| 4,896,303 A | 1/1990 | Leslie et al. | | |
| 5,047,992 A | 9/1991 | Howlett | ............ | 367/31 |
| 5,089,989 A | 2/1992 | Schmidt et al. | ............ | 367/35 |
| 5,229,554 A | 7/1993 | Cole | ............ | 181/106 |
| 5,763,773 A | 6/1998 | Birchak et al. | ............ | 73/152.58 |
| 5,907,131 A | 5/1999 | Tello | | |
| 6,047,602 A | 4/2000 | Lynnworth | | |
| 6,081,116 A | 6/2000 | Wu et al. | ............ | 324/303 |
| 6,176,132 B1 | 1/2001 | MacLauchlan | ............ | 73/290 V |

(Continued)

*Primary Examiner*—Scott A Hughes
(74) *Attorney, Agent, or Firm*—Mossman Kumar & Tyler PC

(57) ABSTRACT

A combined electromagnetic acoustic transducer (EMAT) is disclosed adapted to generate both SH-type acoustic waves and LAMB-type acoustic waves in a conductive casing, surroundings of which are to be analyzed. The transducer comprises one magnet assembly and two RF coils implemented as multi-layer printed circuit board. Each coil is used to generate or receive acoustic signals of one wave type. Compared to using two single-wave-type transducers the combined EMAT significantly reduces total attraction force to the casing and, correspondingly, simplifies mechanics of the measurement tool. It is emphasized that this abstract is provided to comply with the rules requiring an abstract which will allow a searcher or other reader to quickly ascertain the subject matter of the technical disclosure. It is submitted with the understanding that it will not be used to interpret or limit the scope or meaning of the claims.

20 Claims, 12 Drawing Sheets

U.S. PATENT DOCUMENTS

| | | |
|---|---|---|
| 6,179,084 B1 | 1/2001 | Yamamoto et al. .......... 181/106 |
| 6,219,301 B1 | 4/2001 | Moriarty |
| 6,373,245 B1 * | 4/2002 | Kwun et al. ................ 324/240 |
| 6,424,150 B2 * | 7/2002 | Kwun et al. ................ 324/216 |
| 6,575,043 B1 | 6/2003 | Huang et al. |
| 6,666,095 B2 | 12/2003 | Thomas et al. |
| 6,839,640 B2 | 1/2005 | Ohtani |
| 6,850,462 B2 | 2/2005 | McDaniel et al. |
| 6,920,792 B2 * | 7/2005 | Flora et al. .................... 73/622 |
| 6,951,133 B2 | 10/2005 | Passarelli, Jr. |
| 7,024,935 B2 | 4/2006 | Paige et al. .................... 73/643 |
| 7,149,146 B2 | 12/2006 | Kuijk et al. |
| 7,165,453 B2 * | 1/2007 | Flora et al. ................... 367/168 |
| 7,311,143 B2 | 12/2007 | Engels et al. |
| 7,406,873 B2 * | 8/2008 | Paige et al. .................... 73/643 |
| 2003/0043055 A1 | 3/2003 | Schultz et al. ........... 340/856.3 |
| 2004/0117119 A1 | 6/2004 | West et al. ..................... 702/6 |
| 2006/0198243 A1 * | 9/2006 | Tang et al. ..................... 367/35 |

\* cited by examiner

COMBINED ELECTRO-MAGNETIC ACOUSTIC TRANSDUCER

CROSS REFERENCE TO RELATED APPLICATIONS

This patent application is a continuation-in-part of U.S. patent application Ser. No. 10/971,485 filed on Oct. 22, 2004, which is a continuation-in-part of U.S. patent application Ser. No. 10/802,612 filed on Mar. 17, 2004. This patent application is also a continuation-in-part of U.S. patent application Ser. No. 11/070,037 filed on Mar. 2, 2005.

BACKGROUND OF THE DISCLOSURE

1. Field of the Invention

The invention relates generally to the field evaluating the integrity of bonds that adhere wellbore casing to a wellbore. More specifically, the present invention relates to a method and apparatus of producing and detecting acoustic forces within a wellbore casing to evaluate the integrity of the casing.

2. Description of Related Art

As illustrated in FIG. 1 wellbores typically comprise casing 8 set within the wellbore 5, where the casing 8 is bonded to the wellbore by adding cement 9 within the annulus formed between the outer diameter of the casing 8 and the inner diameter of the wellbore 5. The cement bond not only adheres to the casing 8 within the wellbore 5, but also serves to isolate adjacent zones (e.g. $Z_1$ and $Z_2$) within an earth formation 18. Isolating adjacent zones can be important when one of the zones contains oil or gas and the other zone includes a non-hydrocarbon fluid such as water. Should the cement 9 surrounding the casing 8 be defective and fail to provide isolation of the adjacent zones, water or other undesirable fluid can migrate into the hydrocarbon producing zone thus diluting or contaminating the hydrocarbons within the producing zone, and increasing production costs, delaying production or inhibiting resource recovery.

To detect possible defective cement bonds, downhole tools 14 have been developed for analyzing the integrity of the cement 9 bonding the casing 8 to the wellbore 5. These downhole tools 14 are lowered into the wellbore 5 by wireline 10 in combination with a pulley 12 and typically include transducers 16 disposed on their outer surface formed to be acoustically coupled to the fluid in the borehole. These transducers 16 are generally capable of emitting acoustic waves into the casing 8 and recording the amplitude of the acoustic waves as they travel, or propagate, across the casing 8. Characteristics of the cement bond, such as its efficacy, integrity and adherence to the casing, can be determined by analyzing characteristics of the acoustic wave such as attenuation. Typically the transducers 16 are piezoelectric devices having a piezoelectric crystal that converts electrical energy into mechanical vibrations or oscillations transmitting acoustic wave to the casing 8. Piezoelectric devices typically couple to a casing 8 through a coupling medium found in the wellbore. Coupling mediums include liquids that are typically found in wellbores. When coupling mediums are present between the piezoelectric device and the casing 8, they can communicate the mechanical vibrations from the piezoelectric device to the casing 8. However, lower density fluids such as gas or air and high viscosity fluids such as some drilling mud may not provide adequate coupling between a piezoelectric device and the casing 8. Furthermore, the presence of sludge, scale, or other like matter on the inner circumference of the casing 8 can detrimentally affect the efficacy of a bond log acquired with a piezoelectric device. Thus for piezoelectric devices to provide meaningful bond log results, they must cleanly contact the inner surface of the casing 8 or be employed in wellbores, or wellbore zones, having liquid within the casing 8. Another drawback faced when employing piezoelectric devices for use in bond logging operations involves the limitation of variant waveforms produced by these devices. Fluids required to couple the wave from the transducer to the casing only conduct compressional waves, thus limiting the wave types that can be induced in or received from the casing. A great deal of information is derivable from variant acoustical waveforms that could be used in evaluating casing, casing bonds, and possibly even conditions in the formation 18. Therefore, there exists a need to conduct bond logging operations without the presence of a particular couplant. A need exists for a bond logging device capable of emitting and propagating into wellbore casing numerous types of waveforms, and recording the waveforms.

Electromagnetic-acoustic transducers (EMATs) have been used in non-destructive testing. An EMAT acts through the following physical principles. When a wire is placed near the surface of an electrically conducting object and is driven by a current at the desired ultrasonic frequency, eddy currents are induced in a near surface region of the object. If a static magnetic field is also present, these eddy currents experience Lorentz forces. These forces cause an acoustic excitation in the object. In a reciprocal use, an electric signal will be generated in the wire as a result of acoustic excitation in a metal placed close to a permanent magnet. Attenuation and/or reflection of the acoustic waves bear information on the defects and surroundings of the object. An EMAT is typically designed to producing a single waveform, such as shear horizontal waves (SH) or Lamb waves.

Various EMAT design configurations have been proposed. U.S. Pat. No. 4,296,486 to Vasile discloses an EMAT including a source of magnetic flux for establishing a static magnetic field, an electrical conductor for conducting an alternating current in the static magnetic field, and an electrically conductive nonmagnetic shield disposes between the source of magnetic flux and the conductor. U.S. Pat. No. 7,024,935 to Paige et al. discloses an EMAT including a magnetic unit arranged to be moved relative to the material under test to magnetize a surface layer of the material, and an electrical winding supplied by an alternating current source, the magnetic unit and the electric winding, in use, being applied in sequence to the material under test whereby the electrical winding is positioned adjacent the material subsequent to magnetization thereof by the magnetic unit, the alternating magnetic flux created by the winding interacting with the remanent magnetization of the material to create ultrasonic vibration of the material.

If different excitation modes are used to characterize the object, then an array of two or more transducers is generally used. The total attraction force between the object and the array of transducers may dramatically complicate mechanics related to placing and moving the array with respect to the object.

Therefore, there exists a need for a device and method to perform acoustic testing in a borehole casing that reduces the amount of placing and moving of the transducers with respect to the object being examined.

SUMMARY OF THE DISCLOSURE

One embodiment disclosed herein is an apparatus configured for use with an electrically conducting material. The apparatus includes a magnet assembly including a plurality of magnets with alternating polarization in a direction substantially orthogonal to a first direction of a body of the electrically conducting material. The apparatus includes a first conductor configured to carry a first current in a direction substantially parallel to the first direction and generate a shear wave in the body upon passage of the first current, a second conductor configured to carry a second current in a direction substantially orthogonal to the first direction and substantially orthogonal to the direction of polarization of the plurality of magnets and generate a Lamb waves upon passage of the second current. The apparatus also includes a receiving transducer configured to produce signals responsive to the generated shear wave and the generated Lamb wave. The apparatus also includes a processor configured to use the produced signals to estimate a property of the received shear wave and the received Lamb wave, and recorded the estimated property on a suitable medium. The electrically conducting material may be a tubular conveyed in a borehole and the first direction may be an axis of the tubular. The polarity of the magnets may be arranged so that the alternating polarizations formed a checkerboard pattern. The first conductor may be further configured to provide rows of the first current alternately carried in opposing directions along the magnet assembly. The second conductor may include at least one crossover portion configured to maintain the generated Lamb wave in two adjacent regions of opposing magnetic polarization. The crossover portion may be configured to switch positions of a pair of wires. The first and second conductors may be configured to be implemented as a printed circuit board. The property may be selected from velocity and/or attenuation. The receiving transducer may further include a magnet assembly including a plurality of magnets with alternating polarizations in a direction substantially orthogonal to the first direction, a first conductor configured to generate a first current in response to a received shear wave, and a second conductor configured to generate a second current in response to a received Lamb wave.

Another disclosed embodiment is a method of generating acoustic waves in an electrically conducting material. The method includes providing a magnet assembly including a plurality of magnets alternating polarization in a direction substantially orthogonal to a first direction of a body of the electrically conducting material. The method further includes conveying a first current in a direction substantially parallel to the first direction to generate a shear wave in the electrically conducting material, conveying a second current in a direction substantially orthogonal to the first direction and substantially orthogonal to this direction of polarization of the plurality of magnets to generate a Lamb wave, producing signals responsive to the generated shear wave and the generated Lamb wave at a receiving transducer, estimating a property of the received shear wave and the received Lamb wave from the produced signals, and recording the estimated property on a suitable medium. The electrically conducting material may be a tubular conveyed in a borehole and the first direction may be an axis of the tubular. Providing a magnet assembly may further include arranging the plurality of magnets so that the alternating polarizations formed a checkerboard pattern. Conveying the first current may further involve conveying the current in opposite directions. Conveying the second current may include using a conductor having a crossover portion. The crossover portion maintains the generated Lamb wave in two adjacent regions of opposing magnetic polarization. The property may be velocity and/or attenuation. Producing the signals may include providing a magnet assembly including a plurality of magnets with alternating polarization in a direction substantially orthogonal to the first direction, generating a first current in a first conductor in response to the received shear wave, and generating a second current in a second conductor in response to the received Lamb wave.

Another embodiment is a computer-readable medium for use with a tool for evaluating an electrically conducting material. The tool includes a magnet assembly including a plurality of magnets with alternating polarization substantially orthogonal to a first direction of a body of the electrically conducting material, a first conductor configured to carry a first current in a direction substantially parallel to the first direction and generate a shear wave in the body upon passage of the first current, a second conductor configured to carry a second current in a direction substantially orthogonal to the first direction and substantially orthogonal to the direction of polarization of the plurality of magnets and generate Lamb wave upon passage of the second current, and a receiving transducer configured to produce signals responsive to the generated shear wave and the generated Lamb wave. The medium includes instructions which enable a processor to estimate a velocity of the generated shear wave and the generated Lamb wave from the produced signals and record the estimated velocities on a suitable medium. The medium may include a ROM, and EPROM, an EEPROM, a flash memory, and/or an optical disk.

BRIEF DESCRIPTION OF THE DRAWINGS

The present invention and its advantages will be better understood by referring to the following detailed description and the attached drawings in which.

Figure 1:
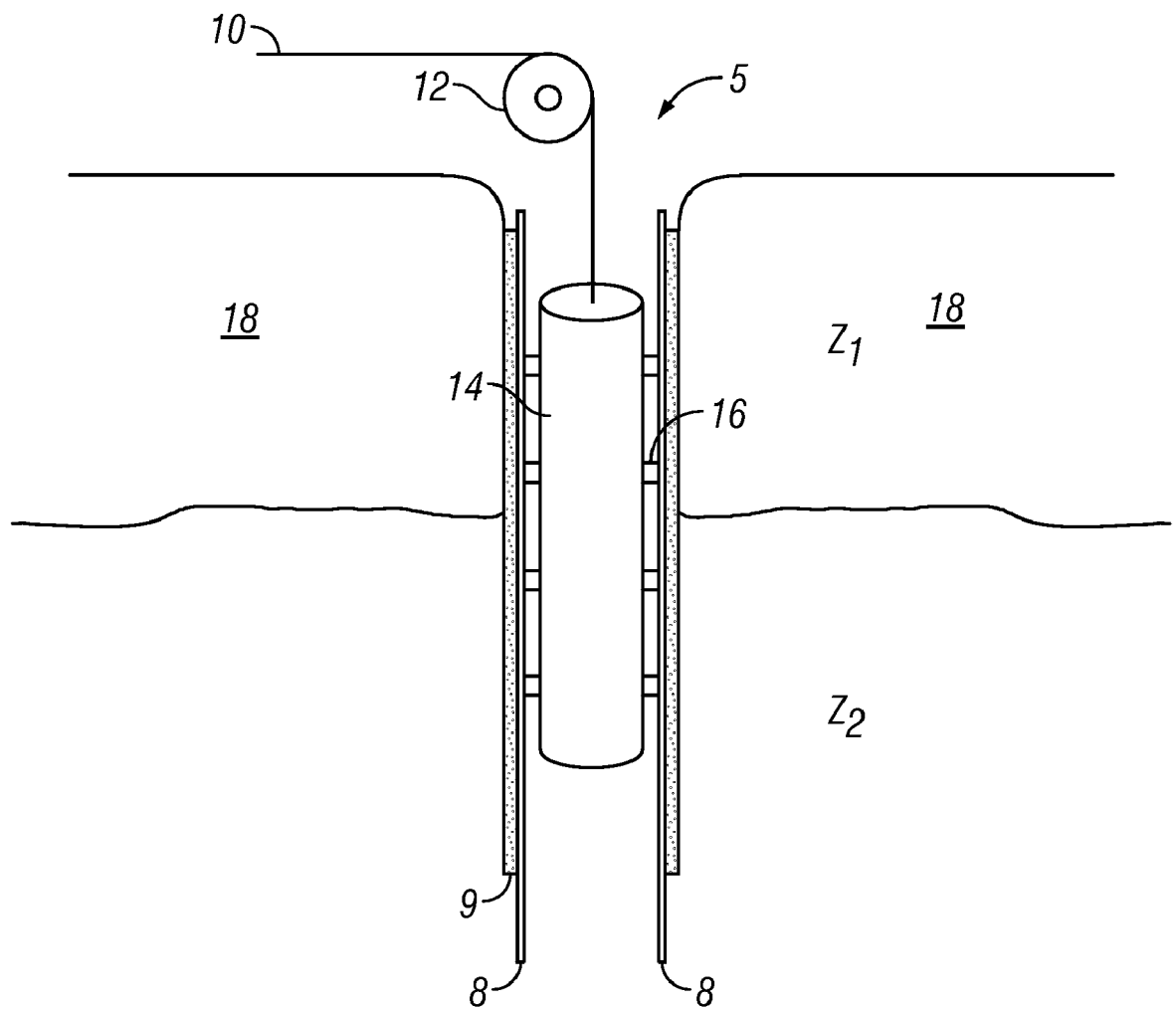
FIG. 1 depicts a partial cross section of prior art downhole cement bond log tool disposed within a wellbore.

While the invention will be described in connection with its preferred embodiments, it will be understood that the invention is not limited thereto. It is intended to cover all alternatives, modifications, and equivalents which may be included within the spirit and scope of the invention, as defined by the appended claims.

DETAILED DESCRIPTION OF THE INVENTION

The present disclosure describes a combined electromagnetic acoustic transducer (EMAT) adapted to generate both shear horizontal type (SH-type) acoustic waves and Lamb-type acoustic waves in a conductive casing. The transducer comprises one magnet assembly and two radio frequency (RF) coils implemented as a multi-layer printed circuit board. Each coil is used to generate or receive acoustic signals of one wave type. Compared to using two single-wave-type transducers the combined one significantly reduces the total attraction force between the casing and the EMAT, and correspondingly simplifies the mechanical aspects of the measurement tool.

Lamb waves are complex vibrational waves that travel through the entire thickness of a material, such as a metal plate. While different modes of waveforms are possible with Lamb waves, two of the most common types of Lamb waves are symmetric and anti-symmetric. In a symmetric Lamb wave, particle movement within the plate undergoes both compression and rarefaction as the wave passes along the plate. The compression and rarefaction particle movement of the symmetric Lamb wave within the plate is primarily in the vertical direction. The anti-symmetric Lamb wave is a longitudinal shear wave that is vertically polarized such that the particle movement is also perpendicular to the plane of the plate. However the particle movement of the anti-symmetric Lamb wave is generally in the same direction and thus does not experience the compression and rarefaction of the symmetric Lamb wave.

Changes in ultrasonic wave propagation speed, along with energy losses from interactions with materials microstructures are often used to nondestructively gain information about properties of the material. An ultrasonic wave, such as a Lamb wave or a shear horizontal (SH) wave, may be created in a material sample, such as a solid beam, by creating an impulse at one region of the sample. As the wave propagates through the sample, residual stresses and other material defects affect the wave. Once the affected wave is recorded, the nature of the stresses of the material can be determined. Measurements of sound velocity and ultrasonic wave attenuation can be related to the elastic properties that can be used to characterize the texture of polycrystalline metals.

The amount of attenuation can depend on how an acoustic wave is polarized and the coupling condition between the casing and the cement. Typical downhole tools having acoustic wave transducers generate acoustic waves that are polarized perpendicular to the surface of the casing. Such waves are referred to as compression/shear or P-SV waves since the particle motion direction of either the compressional (P) or the shear (S) component of the acoustic wave is in a vertical (V) plane perpendicular to the casing. The attenuation of the acoustic wave as it propagates along the surface of the casing depends on the condition of the cement bond and is also dependent on the type of cement disposed between the casing and the formation. More specifically, as the acoustic wave propagates along the length of the casing, the wave loses, or leaks, energy into the formation through the cement bond—it is this energy loss that produces the attenuation of the acoustic wave. Conversely, when the casing is not bonded, a condition also referred to as "free pipe," the micro-annulus fluid behind the casing does not provide for any shear coupling between the casing and the formation. Loss of shear coupling significantly reduces the compressional coupling between the casing and the formation. This result occurs since fluid has no shear modulus as well as a much lower bulk modulus in relation to cement. Because of these physical characteristics of fluid, the entire SV component of the P-SV wave and a large portion of the P component of the P-SV wave do not propagate outside of the casing and thus experience a much reduced attenuation.

The present invention comprises a downhole tool disposable within a wellbore comprising a magnetically coupling transducer, a transmitter and/or receiver comprising a coil and a magnet. The term "magnet" as used in reference to the present invention is used in its commonly-understood manner to mean any device that creates a magnetic field or that produces a magnetic field external to itself. A magnet may be a permanent magnet, a direct current electromagnet, an alternating current electromagnet, or any other device creating a magnetic field. The coil and the magnet are combinable to produce an energy field capable of inducing or measuring waveforms within the wellbore casing. Optionally, the magnetic coupling transducer is an electromagnetic acoustic transducer. The magnetic coupling transmitter and the receiver can be disposed onto the downhole tool housing and the transmitter disposed onto the wellbore casing. The tool comprises a receiver capable of sensing the waveforms within the wellbore casing. The downhole tool can further comprise a sonde formed to house the magnetic coupling transducer, a transmitter and receiver; the tool can be insertable within the wellbore casing. Optionally included with the tool is an electrical source capable of providing an electrical current to the coil, which may be activated electrically and/or electrically modulated. The downhole tool may traverse substantially the entire cased portion of a wellbore, or only a portion of the cased wellbore, with the transducer in contact and magnetically coupled to the wellbore casing.

The magnetic coupling transmitter/receiver is capable of forming or receiving a wave within the casing. Such a wave may include compressional waves, shear waves, transversely polarized shear waves, Lamb waves, Rayleigh waves, and combinations thereof. The magnetic coupling transmitter and the receiver can be disposed at substantially the same radial location with respect to the axis of the housing. Alternatively, the magnetic coupling transmitter and the receiver can be disposed at varying radial locations with respect to the axis of the housing. Alternatively the magnetic coupling transmitter and the receiver can be disposed at substantially the same location along the length of the housing. The magnetic coupling transmitter and the receiver can be disposed at different locations along the length of the housing. Two or more rows of acoustic devices can be disposed radially with respect to the axis of the housing, wherein the acoustic devices include at least one magnetic coupling transmitter and at least one receiver. Optionally, these rows can be staggered or can be substantially helically arranged. Alternatively, any magnet/coil pair may serve as both a transmitter and a receiver at different times during the data acquisition or measurement process.

The present invention provides a method of inspecting the casing bond of a casing disposed within a wellbore. The method can involve combining a magnetic field with an electrical field to induce waveforms within the casing where the waveforms pass through the wellbore casing; sensing the waveforms propagating through the wellbore casing; and analyzing the waveforms propagating through the wellbore casing to determine the integrity of the casing bond. The method of the present invention can further comprise forming the magnetic field and the electrical field with a magnetically coupled transducer and receiving the reflected waves with a receiver. The method can also include adding an electrical source to the coil.

Additionally, the magnetically coupled transducer of the present method can comprise a magnet and a coil, wherein the magnet is one or more of a permanent magnet, a direct current electro-magnet, and an alternating current electro-magnet. Further, the magnetically coupled transducer can be an electromagnetic acoustic transducer. With regard to the present method, the waves induced by the combination of the magnetic field with the electrical field include compressional waves, shear waves, Lamb waves, Rayleigh waves, and combinations thereof. Additionally, the method of the present invention may comprise the magnetically coupled transducer with a receiver mounted to a sonde disposed within the casing, wherein the sonde is in operative communication with the surface. The magnetic coupling transmitter and the receiver can be disposed at substantially the same radial location with respect to the axis of the casing. Optionally, in the method of the present invention, the magnetic coupling transmitter and the receiver can be disposed at varying radial locations with respect to the axis of the casing. Further, the magnetically coupling transmitter and the receiver can be disposed at substantially the same location along the length of the casing or can be disposed at different locations along the length of the casing. The method can further include disposing two or more rows radially with respect to the axis of the casing, wherein each of the two or more rows includes at least one magnetic coupling transmitter and at least one receiver, each of the two or more rows can be staggered or can be helically arranged. Accordingly, one of the advantages provided by the present invention is the ability to conduct casing bond logging activities in casing irrespective of the type of fluid within the casing and irrespective of the conditions of the inner surface of the casing. An additional advantage of the present invention is the ability to induce and then detect numerous waveforms within the casing, combinations of waveforms within the casing, and simultaneous waveforms within the casing.

Figure 2B:
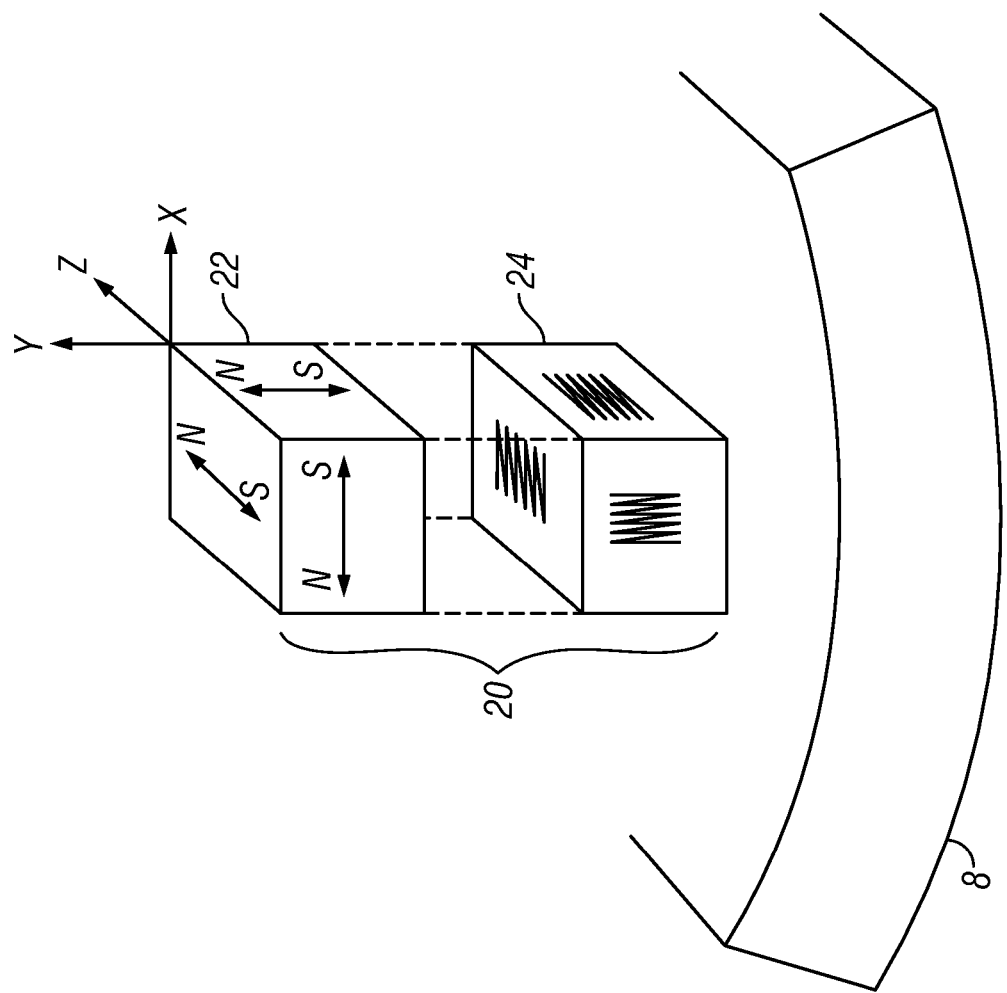
FIGS. 2A-2B schematically illustrate a magnetic coupling transmitter disposed to couple to a section of casing.
Figure 2A:
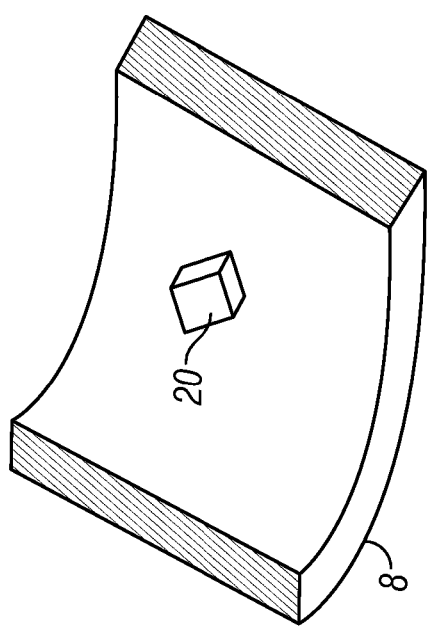

As illustrated in FIG. 2A, a magnetically coupled transducer 20 is positioned at any desired attitude proximate to a section of casing 8. For the purposes of clarity, only a portion of the length and diameter of a section of casing 8 is illustrated and the magnetically coupled transducer 20 is shown schematically in both FIG. 2A and FIG. 2B. The magnetically coupled transducer 20 may be positioned within the inner circumference of the tubular casing 8, but the magnetically coupled transducer 20 can also be positioned in other areas.

For any particular transducer 20, more than one magnet (of any type for example permanent, electro-magnetic, etc.) may be combined within a unit; such a configuration enables inducing various waveforms and facilitating measurement and acquisition of several waveforms. A transducer 20 capable of transmitting or receiving waveforms in orthogonal directions is schematically illustrated in FIG. 2B. While a schematic magnet 22 with orthogonal magnetic fields is illustrated, a single-field relatively large magnet with multiple smaller coils 24 (which coils may be disposed orthogonally) may be employed to form versatile transducers.

In embodiments provided by the present invention that are illustrated schematically in FIGS. 2A and 2B, the magnetically coupled transducer 20 is comprised of a magnet 22 and a coil 24, where the coil 24 is positioned between the magnet 22 and the inner circumference of the casing 8. An electrical current source (not shown) is connectable to the coil 24 capable of providing electrical current to the coil 24. The magnet 22, may be one or more permanent magnets in various orientations or can also be an electro-magnet, energized by either direct or alternating current. FIG. 2B schematically illustrates orthogonal magnetic and coil representations. One or more magnets or coils may be disposed within a downhole tool to affect desired coupling and/or desired wave forms such as the direct inducing of shear waves into casing 8. While the coil is illustrated as disposed between the magnet and the casing, the coil may be otherwise disposed adjacent to the magnet.

The coil 24 may be energized when the magnetically coupled transducer 20 is proximate to the casing 8 to produce acoustic waves within the material of the casing 8. For example the coil may be energized with a modulated electrical current. Thus the magnetically coupled transducer 20 operates as an acoustic transmitter.

The magnetically coupled transducer 20 can also operate as a receiver capable of receiving waves that traversed the casing and cement. The magnetically coupled transducer 20 may be referred to as an acoustic device. As such, the acoustic devices of the present invention function as acoustic transmitters or as acoustic receivers, or as both.

Figure 3:
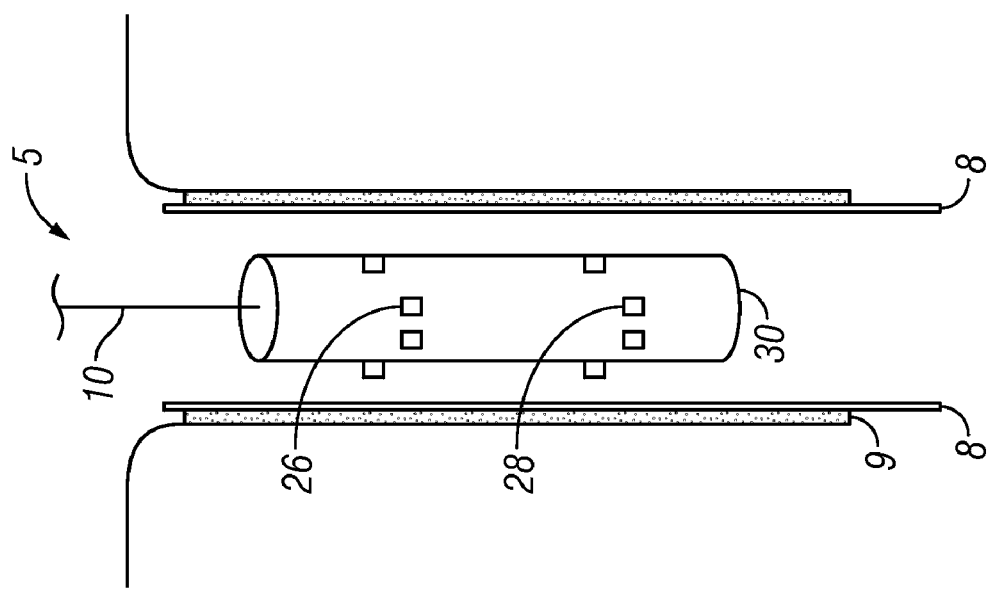
FIG. 3 shows one embodiment of the present invention disposed within a wellbore.

The present invention as illustrated in FIG. 3 provides a sonde 30 shown having acoustic devices disposed on its outer surface. The acoustic devices comprise a series of acoustic transducers, both transmitters 26 and receivers 28, where the distance between each adjacent acoustic device on the same row may be substantially the same. With regard to the configuration of acoustic transmitters 26 and acoustic receivers 28 shown in FIG. 3, while the rows 34 radially circumscribing the sonde 30 can comprise any number of acoustic devices (i.e. transmitters 26 or receivers 28), it is preferred that each row 34 comprise five or more of these acoustic devices (the preference for five or more devices is for devices with the transmitters and receivers radially arranged around the circumference e.g., FIG. 4a). The acoustic transmitters 26 may be magnetically coupled transducers 20 of the type of FIGS. 2A and 2B comprising a magnet 22 and a coil 24. Optionally, the acoustic transmitters 26 can comprise electromagnetic acoustic transducers.

Referring now again to the configuration of the acoustic transmitters 26 and acoustic receivers 28 of FIG. 3, the acoustic transducers comprising transmitters 26 and receivers 28 can be arranged in at least two rows where each row comprises primarily acoustic transmitters 26 and a next adjacent row comprises primarily acoustic receivers 28. Optionally, as shown in FIG. 3, the acoustic devices within adjacent rows in this arrangement are aligned in a straight line along the length of the sonde 30.

While only two circumferential rows 34 of acoustic devices are shown in FIG. 3, variations and placement of transducers and arrangements in rows can be included depending on the capacity and application of the sonde 30. Another arrangement is to have one row of acoustic transducers 26 followed by two circumferential rows of acoustic receivers 28 followed by another row of acoustic transducers 26. As is known in the art, advantages of this particular arrangement include the ability to make a self-correcting acoustic measurement. Attenuation measurements are made in two directions using arrangements of two transmitters and two receivers for acquisition of acoustic waveforms. The attenuation measurements may be combined to derive compensated values that do not depend on receiver sensitivities or transmitter power.

Figure 4A:
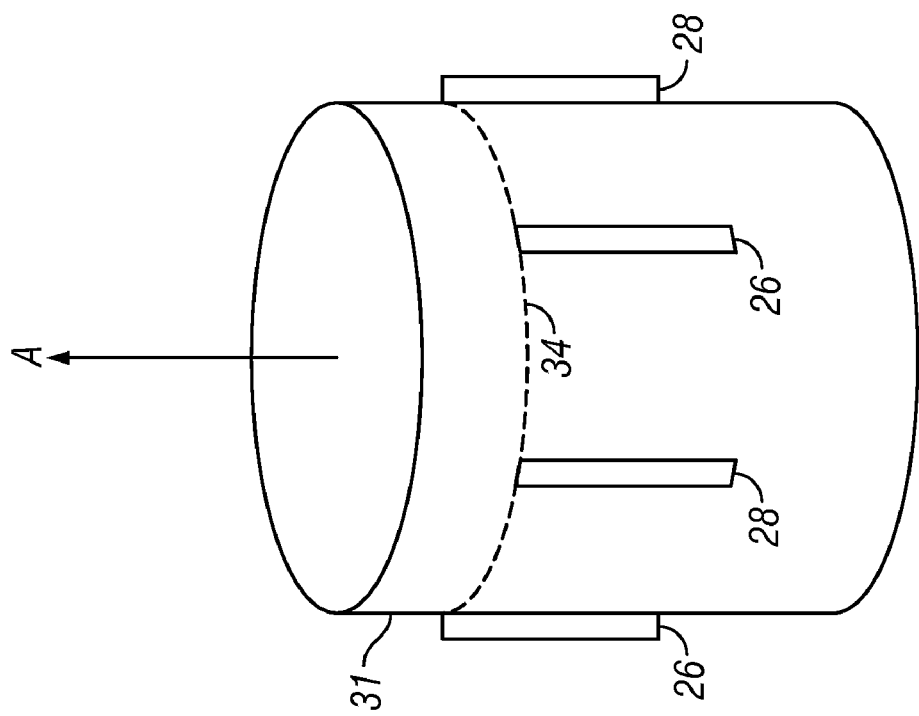
FIGS. 4A-4D depict alternative embodiments of the present invention.

Additional arrangements of the acoustic transducers 26 and acoustic receivers 28 disposed on a sonde 31 are illustrated in a series of non-limiting examples in FIGS. 4A through 4D. In the embodiment of FIG. 4A a row of alternating acoustic transducers, transmitters 26 and receivers 28 are disposed around the sonde 31 at substantially the same elevation. The acoustic devices may be equidistantly disposed around the axis A of the sonde section 31. In an alternative configuration of the present invention shown in FIG. 4B, the acoustic devices are disposed in at least two rows around the axis A of the sonde section 31, but unlike the arrangement of the acoustic devices of FIG. 3, the acoustic devices of adjacent rows are not aligned along the length of the sonde 30, but instead are staggered.

Figure 4C:
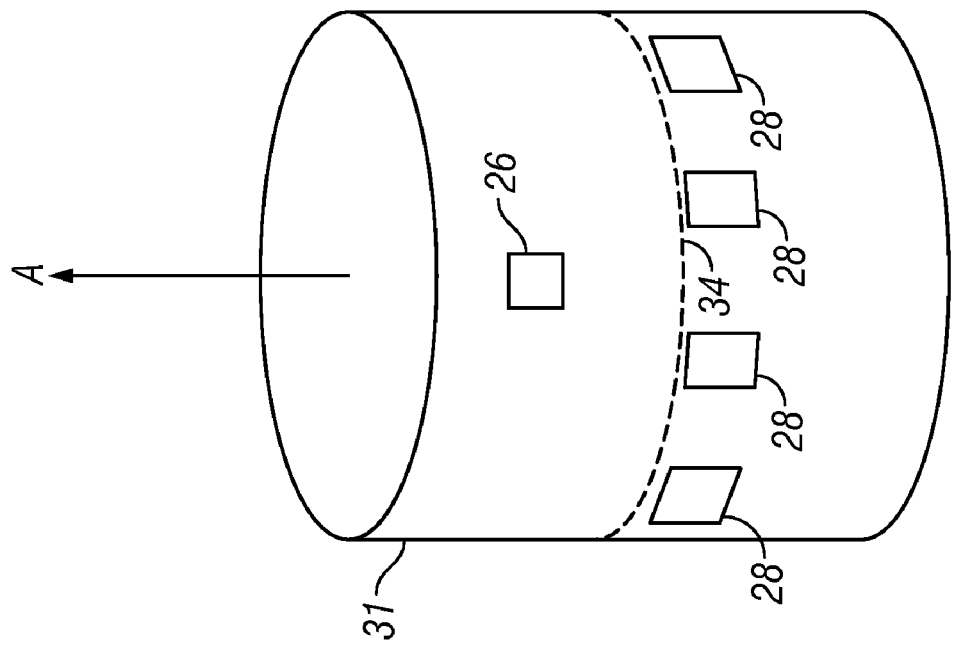
Figure 4B:
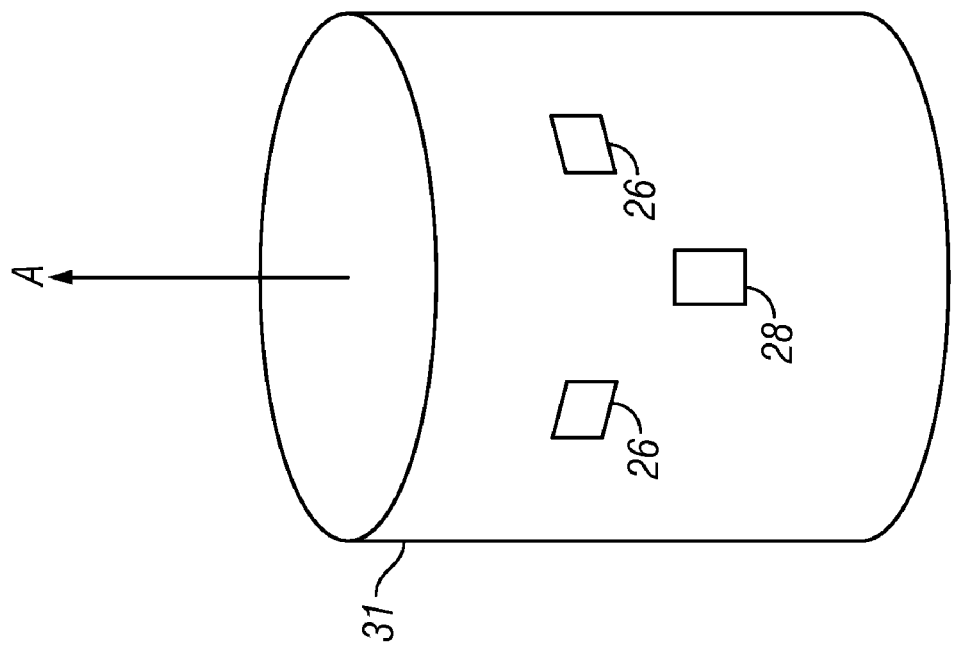
Figure 4D:
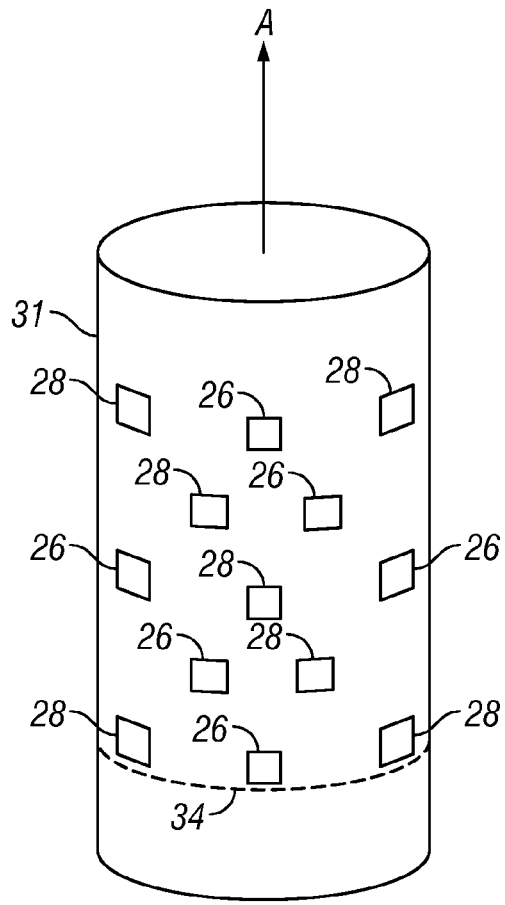

FIG. 4C illustrates a configuration where a single acoustic transmitter 26 cooperates with a group or groups of acoustic receivers 28. Optionally the configuration of FIG. 4C can have from 6 to 8 receivers 28 for each transmitter 26. FIG. 4D depicts rows of acoustic transducers where each row comprises a series of alternating acoustic transducers 26 and acoustic receivers 28. The configuration of FIG. 4D is similar to the configuration of FIG. 4B in that the acoustic devices of adjacent rows are not aligned but instead are staggered. It should be noted however that the acoustic devices of FIG. 4D may be staggered in a way that a substantially helical pattern (44) is formed by acoustic devices around the sonde. The present invention is not limited in scope to the configurations displayed in FIGS. 4A through 4D, and other arrangements will occur to practitioners of the art and are contemplated within the scope of the present invention.

In operation of one embodiment of the present invention, a series of acoustic transmitters 26 and acoustic receivers 28 are included on a sonde 30 (or other downhole tool). The sonde 30 is then secured to a wireline 10 and deployed within a wellbore 5 for evaluation of the casing 8, casing bond, and/or formation 18. When the sonde 30 is within the casing 8 and proximate to the region of interest, the electrical current source can be activated thereby energizing the coil 24. Providing current to the coil 24 via the electrical current source produces eddy currents within the surface of the casing 8 as long as the coil 24 is sufficiently proximate to the wall of the casing 8. It is within the capabilities of those skilled in the art to situate the coil 24 sufficiently close to the casing 8 to provide for the production of eddy currents within the casing 8. Inducing eddy currents in the presence of a magnetic field imparts Lorentz forces onto the particles conducting the eddy currents that in turn causes oscillations within the casing 8 thereby producing waves within the wall of the casing 8. The coil 24 of the present invention can be of any shape, design, or configuration as long as the coil 24 is capable of producing an eddy current in the casing 8.

Accordingly, the magnetically coupled transducer 20 is magnetically "coupled" to the casing 8 by virtue of the magnetic field created by the magnetically coupled transducer 20 in combination with the eddy currents provided by the energized coil 24. Thus one of the many advantages of the present invention is the ability to provide coupling between an acoustic wave producing transducer without the requirement for the presence of liquid medium. Additionally, these magnetically induced acoustic waves are not hindered by the presence of dirt, sludge, scale, or other like foreign material as are traditional acoustic devices, such as piezoelectric devices.

The waves induced by combining the magnet 22 and energized coil 24 propagate through the casing 8. These acoustic waves can further travel from within the casing 8 through the cement 9 and into the surrounding formation 18. At least a portion of these waves can be reflected or refracted upon encountering a discontinuity of material, either within the casing 8 or the area surrounding the casing 8. Material discontinuities include the interface where the cement 9 is bonded to the casing 8 as well as where the cement 9 contacts the earth formation (e.g. $Z_1$ and $Z_2$ of FIG. 1). Other discontinuities can be casing seams or defects, or even damaged areas of the casing such as pitting or corrosion.

As is known, the waves that propagate through the casing 8 and the reflected waves are often attenuated with respect to the wave as originally produced. The acoustic wave characteristic most often analyzed for determining casing and cement adhesion is the attenuation of the transmitted waves that have traversed portions of the casing 8 and/or cement 9. Analysis of the amount of wave attenuation can provide an indication of the integrity of a casing bond (i.e. the efficacy of the cement 9), the casing thickness, and casing integrity. The reflected waves and the waves that propagate through the casing 8 can be recorded by receiving devices disposed within the wellbore 5 and/or on the sonde. The sonde 30 may contain memory for data storage and a processor for data processing. If the sonde 30 is in operative communication with the surface through the wireline 10, the recorded acoustic waves can be subsequently conveyed from the receivers to the surface for storage, analysis and study.

An additional advantage of the present design includes the flexibility of producing and recording more than one type of waveform. The use of variable waveforms can be advantageous since one type of waveform can provide information that another type of waveform does not contain. Thus the capability of producing multiple types of waveforms in a bond log analysis can in turn yield a broader range of bond log data as well as more precise bond log data. With regard to the present invention, not only can the design of the magnet 22 and the coil 24 be adjusted to produce various waveforms, but can also produce numerous wave polarizations.

Figure 5:
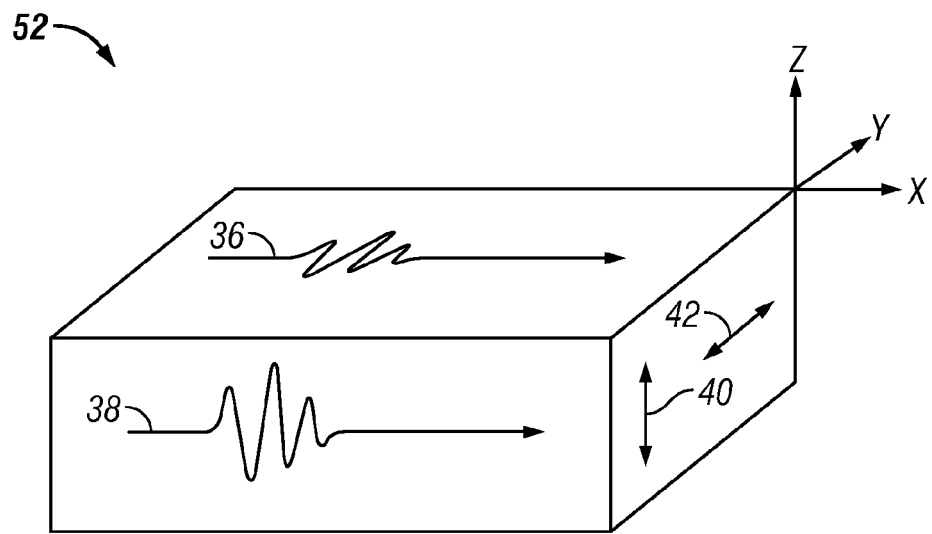
FIG. 5 illustrates shear waveforms propagating through a section of a medium.

FIG. 5 illustrates a vertical shear ($S_V$) waveform 38 and a horizontal shear ($S_H$) waveform 36 that are shown propagating in the x-direction within a wave medium 52. The z-direction has been arbitrarily chosen as up or vertical. The shear waveforms 38 and 36 comprise particle wave motion transverse to the direction of wave propagation. While both waves propagate in the x-direction, they are polarized in different directions. Polarization refers to the direction of particle movement within the medium 52 transverse to the direction of propagation of a wave. A transverse wave is a wave in which the vibrating elements (or particle motion of the medium 32) moves in a direction perpendicular to the direction of advance of the wave. The compressional polarization arrow 40 depicts the direction of polarization of the compressional waveform 38. From this it can be seen that polarization of $S_V$ waves 38 is substantially vertical, or in the z-direction. Conversely, with reference to the shear polarization arrow 42 for the ($S_H$) waveform 36, the direction of polarization is substantially in the y-direction, or normal (horizontally) to the direction of wave propagation.

The shapes and configurations of these waves are illustrated in FIG. 5 as examples of shear waveforms that can be produced by use of a magnetically coupled transducer 20. Moreover, the magnetically coupled transducers 20 are capable of producing additional waveforms, such as Lamb waves, Rayleigh waves. Additionally, the present invention provides for the production of multiple waveforms with the same acoustic transducer. A single transducer of the present invention may be used to produce compressional waves, shear waves, Rayleigh waves, Lamb waves, as well as combinations of these waveforms, and producing these waveforms directly in the casing 8. In contrast, prior art piezoelectric transducers are limited to the production of compressional waveforms into wellbore casing because only compressional waveforms will propagate through a fluid medium.

Figure 6A:
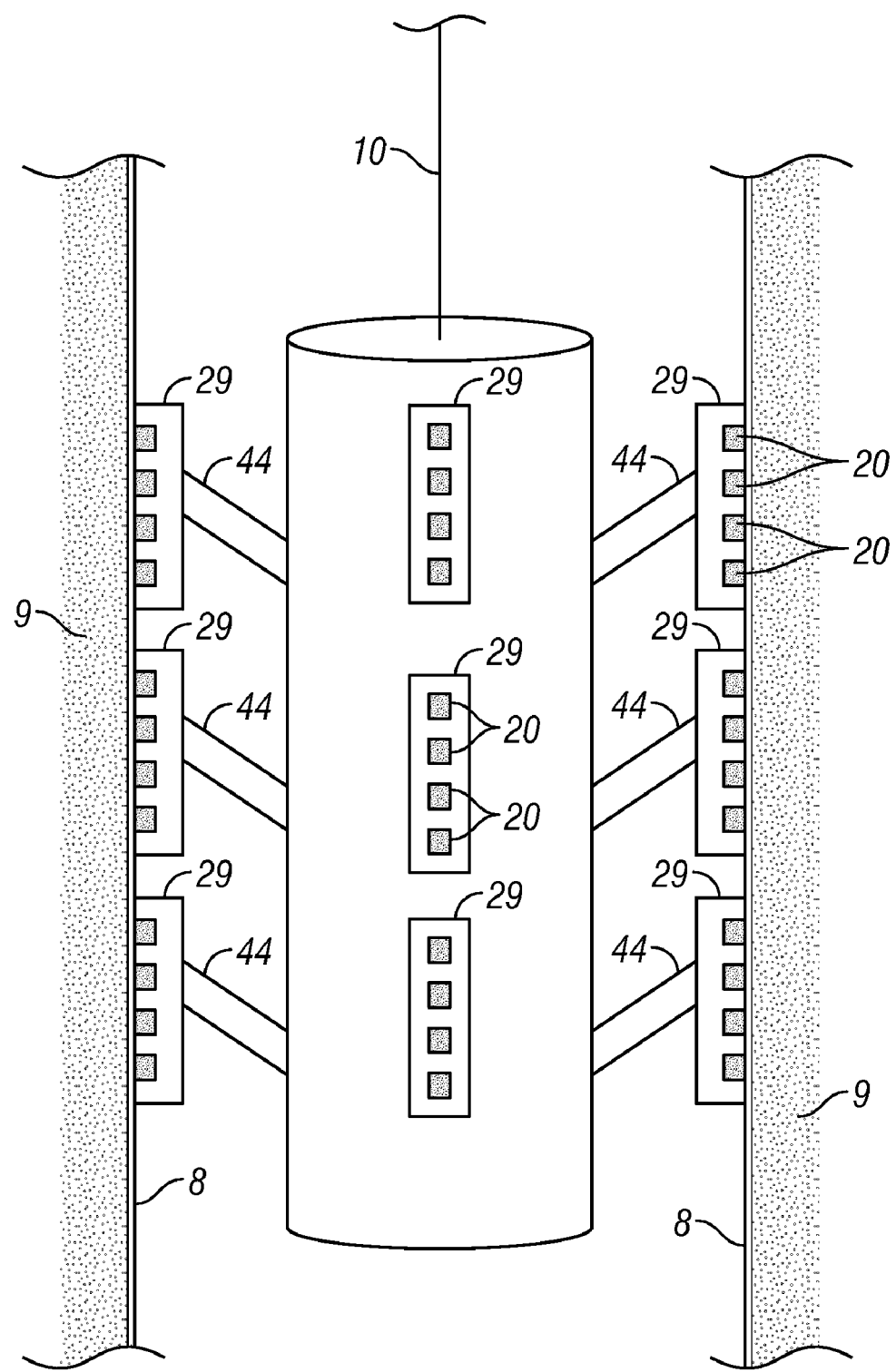
FIG. 6A illustrates an embodiment of the present invention where the transducers are dynamically positioned at or near the well casing inside surface.

FIG. 6A illustrates a bond log tool 32 provided by the present invention where the transducers 20, which may be in a housing or pad 29, are kept in contact with the wellbore casing in substantially all the casing circumference using offset arms 44. Typically high offset arm forces are required which hinder the tool from moving freely. The present invention provides efficient coupling as an electromagnet comprising a vibrating transmitter is dragged along the casing as the tool moves. By vibrating these electromagnets that are magnetically coupled to the casing, the casing physically oscillates. S-waves may be generated by the casing and traverse the cement-bond, cement 9, and underlying formation. The s-waves reflections and refractions may be received with conventional sensors.

FIG. 6A illustrates a pad 29 containing four transducers 20, but the number and positions of pads 29 is not limited to any specific arrangement. The pad 29 with four transducers 20 illustrated in FIG. 6A allows for the implementation of the compensated attenuation arrangement of two receivers between two transmitters, but this is not a limitation and other arrangements may be implemented.

Figure 6B:
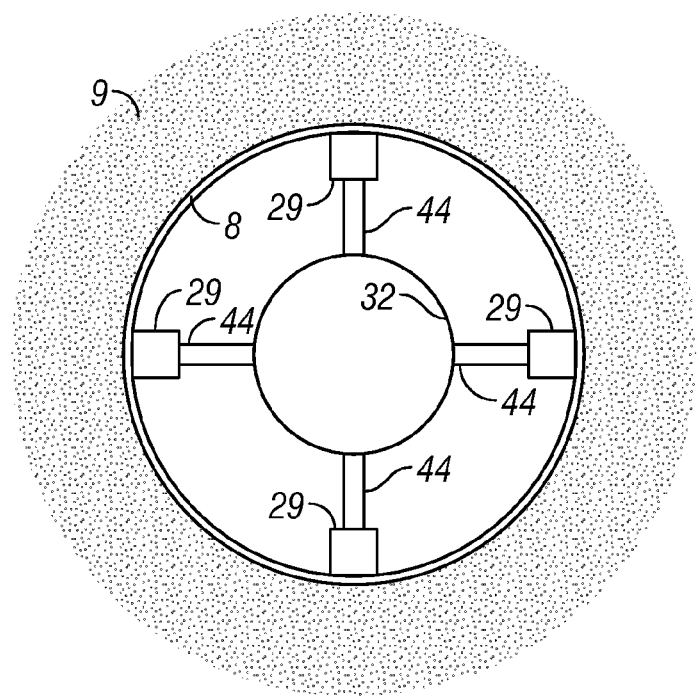
FIG. 6B illustrates a crossectional view of an embodiment of the present invention illustrated in FIG. 6A.
Figure 6C:
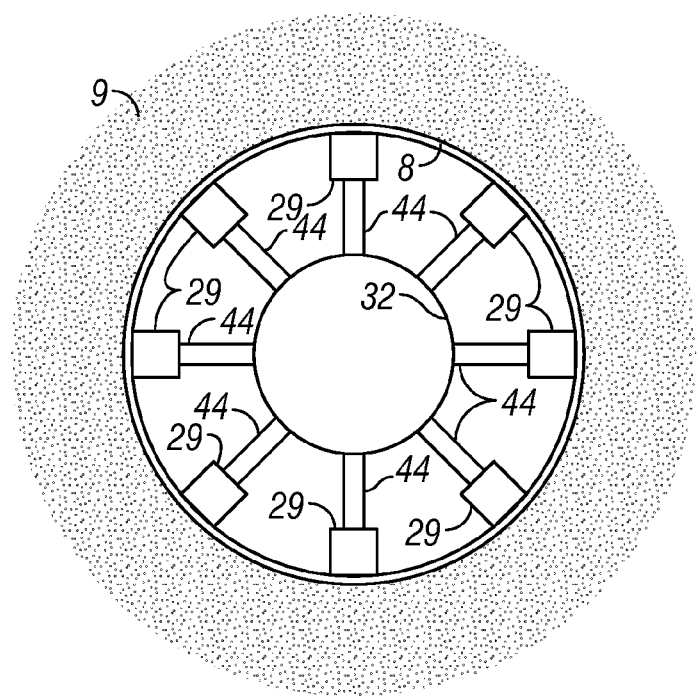
FIG. 6C illustrates a cross-sectional view of an embodiment of the present invention.

FIG. 6B illustrates a cross-sectional view of sonde 32 with offset arms 44 allowing for the magnetically coupling transducers, transmitters or receivers, to contact the casing 8 wall. While four pads 29 with transducers are illustrated in FIG. 6B, FIG. 6C illustrates a sonde providing eight pads that contact the casing 8. An arrangement of six pads with transducers has been found to provide good quantitative analysis of cement bond-to-casing in six 60° segments for 360° coverage around the borehole. Additionally, offset arms may be used to implement other transducer disposition arrangements radially and longitudinally, such as those illustrated in FIGS. 4A-4B.

The present invention offers significant operating advantages over prior art tools due to its insensitivity to heavy or gas-cut borehole fluids, fast formations, temperature and pressure variations, and moderate tool eccentering. The invention is essentially unaffected by various borehole fluids because the offset arms 44 of the tool pads 29 provide for transducers 20 that are coupled magnetically against the casing interior wall where actual measurements are acquired. This enables good results in heavy or gas-cut, mud-filled boreholes. The invention is not affected by "mud" arrivals and can be used effectively in large-diameter pipe and may log a well with a variety of casing sizes on a single pass.

The present invention is effective in environments with fast formations. Using shear waves with short pad spacing does not allow sufficient distance for fast-formation arrivals to overtake casing-borne arrivals.

Figure 7:
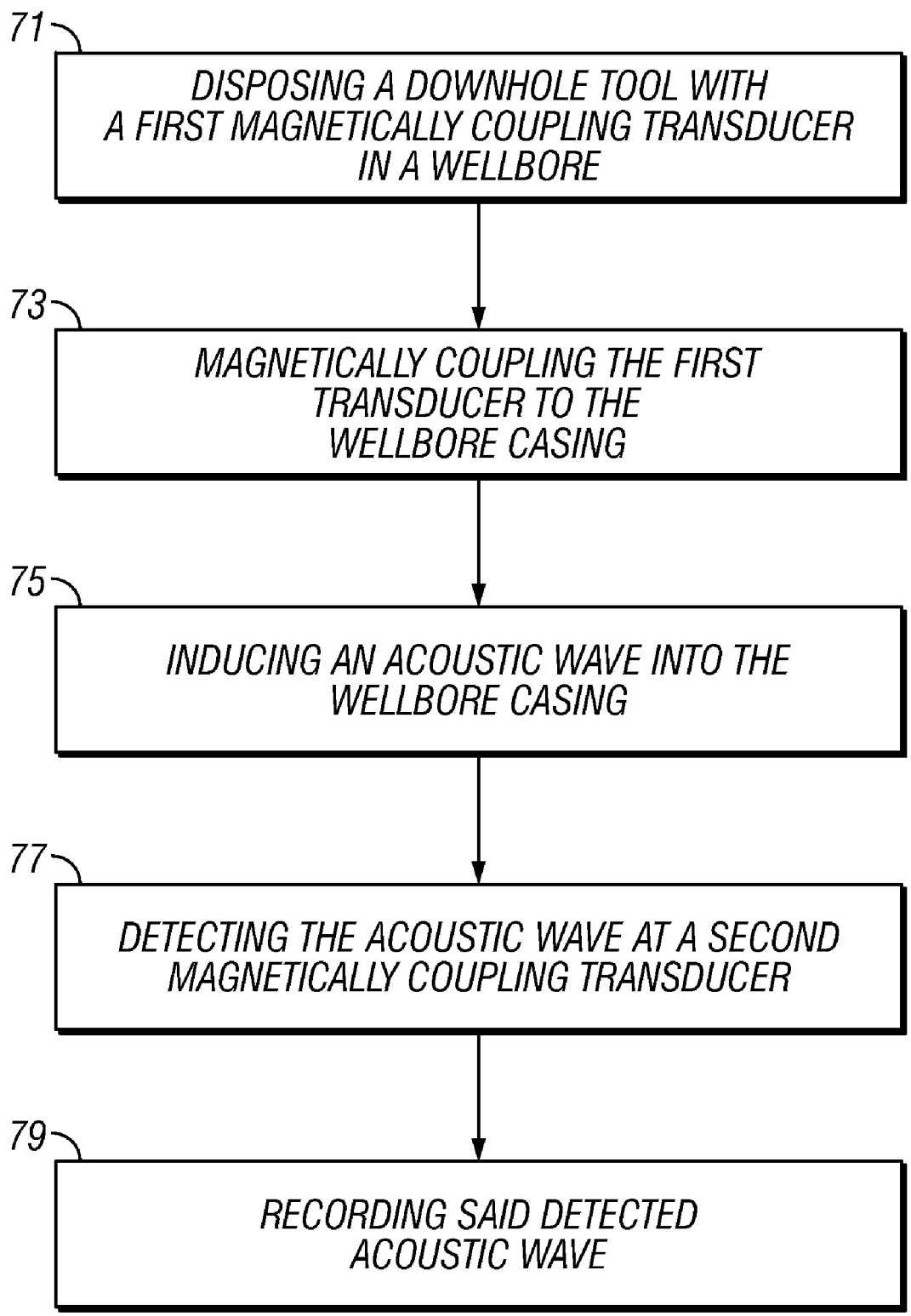
FIG. 7 is a flow chart illustrating a method provided by the present invention.

The present invention further provides for a downhole instrument, which may be sonde 32 of FIG. 6A, which is controlled by an electronic cartridge (not shown) that comprises a downhole microprocessor, a telemetry system which may be digital, and the electronic cartridge may have data storage. Downhole data processing and digital telemetry eliminate distortions that can occur in analog signal transmission by the wireline. Any of the waveforms can be digitized downhole, optionally processed downhole and displayed at the surface FIG. 7 is a flow chart illustrating a method provided by the present invention. A downhole tool, which may be a sonde, is disposed 71 into a wellbore. A magnetically coupling transducer is coupled 73 to the wellbore casing. The downhole tool may comprise extendable arms with pads holding a plurality of transducers for generating and receiving acoustic energy on the wellbore casing. The coupled transducer generates acoustic waves 75 into the wellbore casing. The generated acoustic waves are detected 77 at a second magnetically coupling transducer and the waves are recorded 79. The data recorded may be further processed and/or stored in the downhole tool or transmitted by telemetry to the surface for further processing, analysis and display.

Figure 8A:
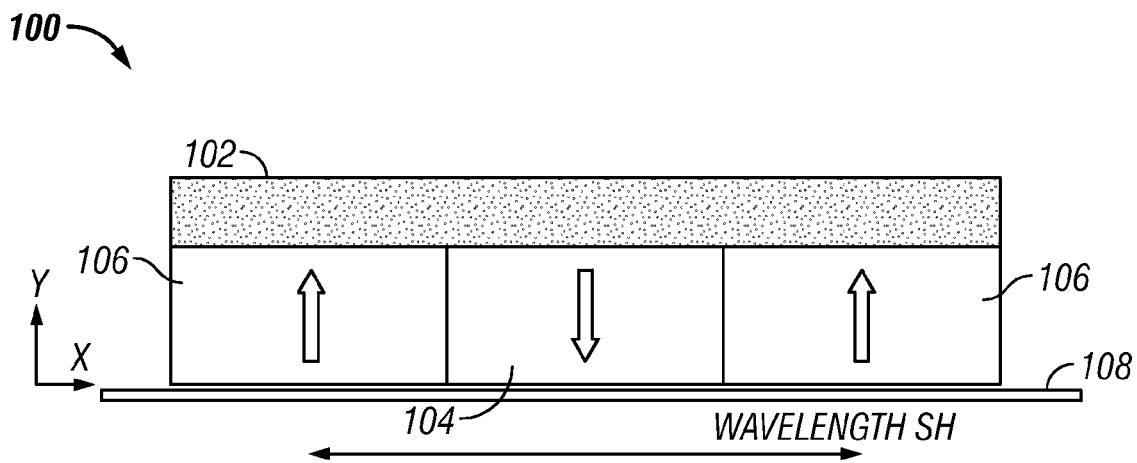
FIGS. 8A-B (Prior Art) show side and bottom views respectively of a standard EMAT used in prior art for generating SH-waves.
Figure 8B:
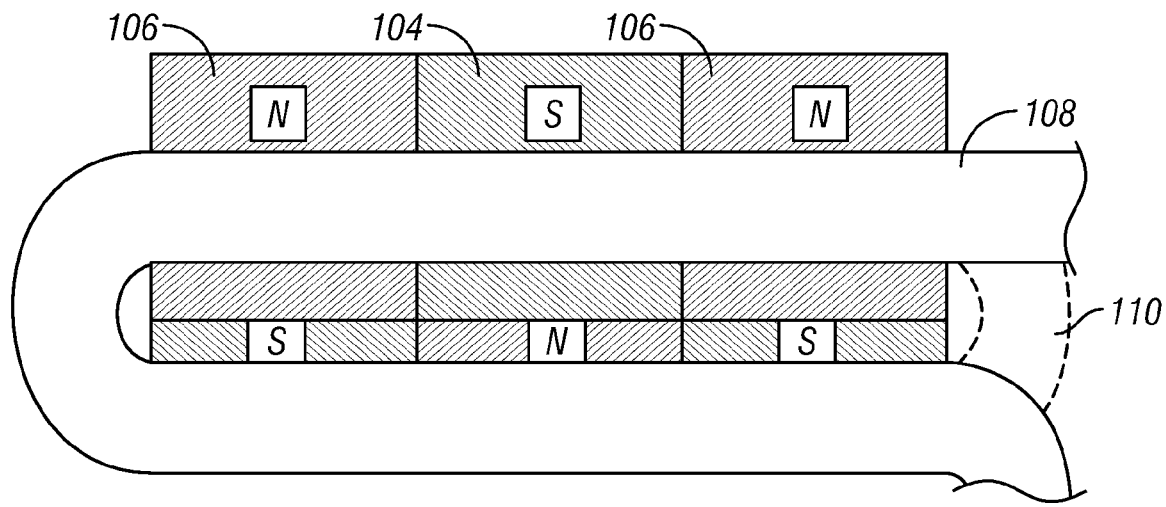

FIGS. 8A and 8B show side and bottom views respectively of a standard EMAT 100 used in prior art for generating SH-waves. The EMAT of FIGS. 8A and 8B comprises magnets 104 and 106 assembled in a magnet array such that the magnetization vectors (as represented by accompanying arrows) have alternating and opposing orientations. The magnet array may be attached to an iron back plate 102 at an attachable face of the magnet array. The iron plate is used to reduce magnetic pole strength on the attachable face of the magnet array. This increases the magnetic field on the operative face of the magnet array opposite to the attachable face. The iron plate may also serve as a supporting device. Wire 108 is placed along an operative face of the magnet array. In one aspect, the EMAT may be operated to produce an SH wave to be transmitted to an examined object (not shown) such as a conductive casing placed against the operative face of the magnet array for examination purposes. Wire 108 may carry an applied current which induces a set of forces by passing the current through the applied magnetic fields of the magnet array. The configuration of the magnet array produces a set of forces which, in combination, produce the SH wave. The wavelength of the SH wave is determined by the separation of the magnets and is generally the distance between the midpoints of magnets 106 adjoining magnet 104, for example. In another aspect, eddy currents circulating in the examined object may induce a current in the wire 108. The eddy currents may result from applied forces on the object. The induced current may be used to determine the size of the eddy currents and thus to determine the applied forces.

FIG. 8B illustrates a bottom view of the EMAT of FIG. 8A. As seen in FIG. 8B, the magnet array extends in two dimensions to form a checkerboard pattern at the operable face. Wire 108 crosses several rows of the magnet array. The wire 108 is formed so as to carry current along alternating rows of the magnet array. The current in the wire reverses directions with each adjacent row. FIG. 8B further shows a return wire 110 for completing an electric circuit.

Figure 8C:
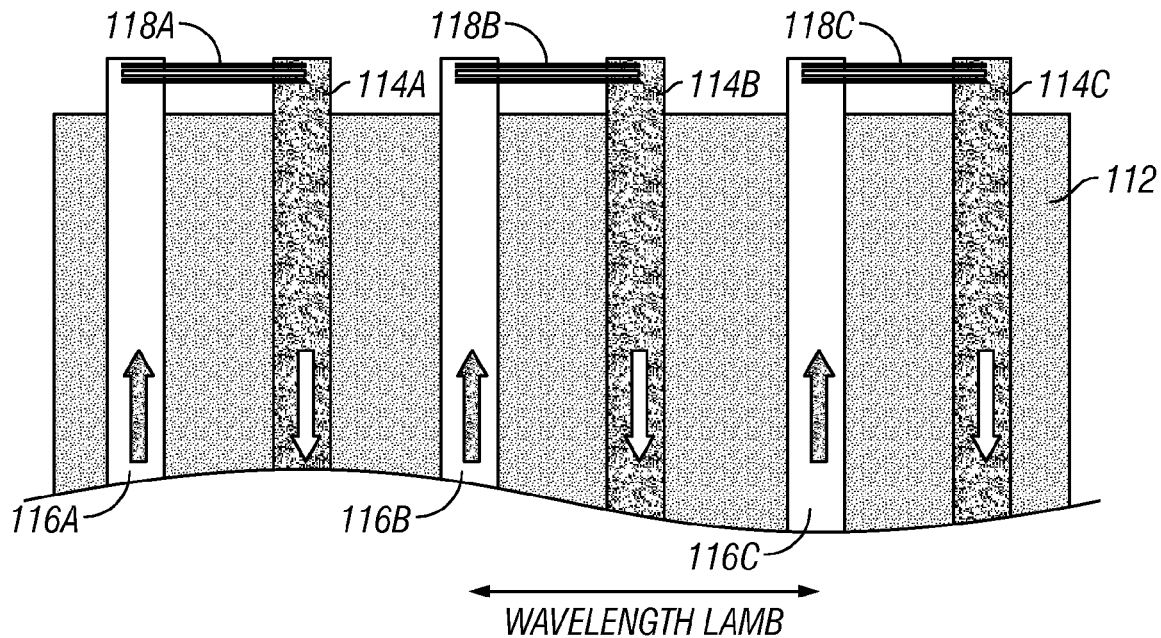
FIG. 8C (Prior Art) shows a bottom view of a portion of a standard EMAT used in prior art for generating a Lamb wave.

FIG. 8C shows a bottom view of a portion of a standard EMAT used in prior art for generating a Lamb wave. The Lamb-wave EMAT comprises a single magnet 112 having a single magnetization direction: perpendicular to face of the drawing. Current is carried along the operative face of the single magnet over a set of wires arranged in parallel rows in the manner shown. The current is carried over wires 114A-C in one direction and over wires 116A-C in the opposite direction. Wires 114A-C and 116A-C are connected by electrical connector 118A-C at their ends. (Wire 114A connects to wire 116A via connector 118A, etc.) At the opposite end (not shown), alternate connections can be made, for example, by connecting wire 114A to wire 116B, etc. In another aspect, the wires 114A-C, 116A-C and connectors 118A-C may be formed as a single wire coil (meander coil). The wavelength of the Lamb wave is generally determinable by the distances between wires carrying current in the same direction, i.e. from wire 116B to wire 116C.

Figure 9A:
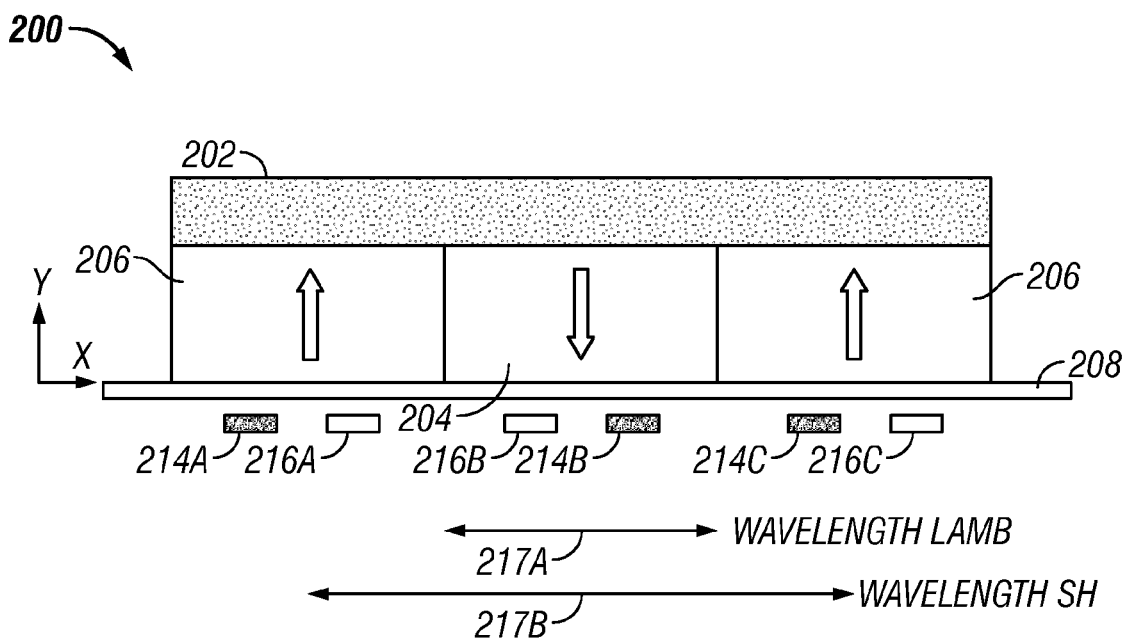
FIGS. 9A-B illustrate an exemplary EMAT configuration of the present disclosure combining SH and Lamb wave production into a single EMAT.
Figure 9B:
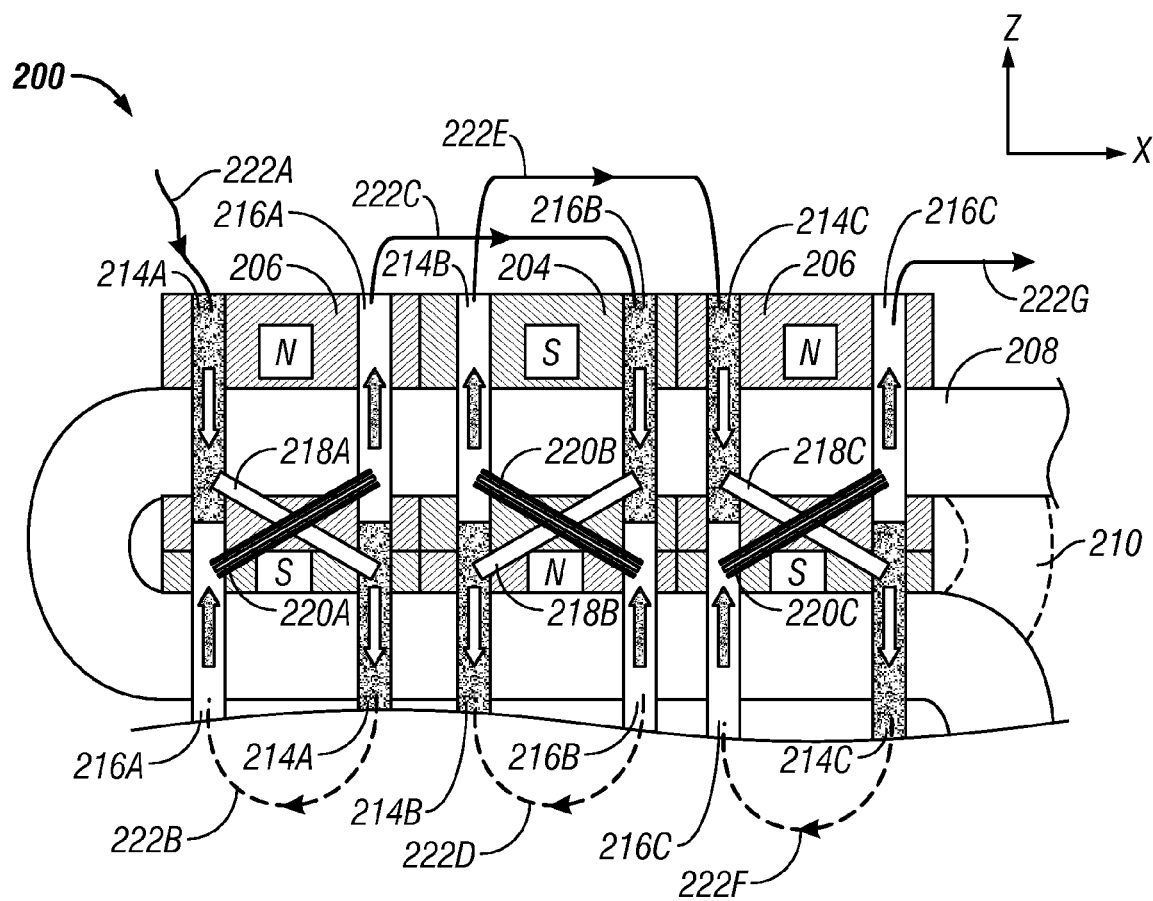

FIGS. 9A and 9B illustrate an exemplary EMAT configuration 200 of the present invention. The exemplary EMAT combines SH and Lamb production into a single transducer. FIG. 9A shows a side view of the exemplary EMAT. The magnet array comprises magnets 204 and 206 oriented so as to have magnetizations vectors (represented by accompanying arrows) alternately oriented in opposing directions along the y-axis. The magnetic array is attached to an iron back plate 202 at an attachable face. A wire configuration is located along the operable face opposite the attachable face. The wire configuration comprises an SH wire 208 for generating and responding to SH waves and Lamb wires 214A-C and 216A-C for generating and responding to Lamb waves. The current in wires 216A-C flow in the opposite direction of the current in wires 214A-C. Lamb wires are paired (i.e., 214A and 216A, 214B and 216B, 214C and 216C), and each pair is associated with a single row of the magnetic assembly. As seen in FIG. 9A, the ordering of the wires in the wire pairs alternate depending on the polarity of the associated applied magnetic field. The number of wires and the number of magnets shown in the magnetic array is for illustrative purposes only and is not meant as a limitation of the invention.

FIG. 9B shows a bottom view of the operable face of the EMAT configuration of FIG. 9A. A magnet array comprises magnets 204 and 206 assembled such that the magnetization directions alternate to produce a checkerboard pattern at the operable face. FIG. 9B shows a detailed view of Lamb wires (214A-C, 216A-C), SH wire 208 and SH-return wire 210. Wires 214A are electrically connected across magnet interface via connector 218A, and wires 216A are connected via connector 220A. Similarly, wires 214B are connected via connector 218B, and wires 216B are connected via connector 220B; and similarly wires 214C are connected via connector 218C, and wires 216C are connected via connector 220C. The current segments 214, 216 may be connected as shown at 222A-G to form a continuous current path. In the illustration of FIG. 9B, Lamb wires carry current along a z-axis. As current flows along the z-axis, the magnetization direction encountered by the current alternately changes between, for instance, a north pole to a south pole. In order to maintain a set of equivalent forces both in the north-pole region and the south-pole region, the direction of currents are switched. An examination of the force equation, Eq. (1), shows that to maintain the same sign of the force when the sign of the magnetic field changes from positive to negative (or negative to positive), the sign of the current must also change.

$$\vec{F} = \vec{J} \times \vec{B} \quad (1)$$

Here $\vec{F}$ is the force per unit volume, $\vec{J}$ is the eddy current density induced in the examined object, the eddy current direction is determined by the direction of the current in the eddy current producing wire, and $\vec{B}$ is the static magnetic field produced by the magnet array at the surface of the examined object.

In other words, wire 214A in the North-pole region produces the same force as wire 216A in the South-pole region. Thus, the Lamb wires are configured and connected in a manner so as to provide a cross-over portion which alternates the directions of the currents between alternating magnetic regions.

An SH wire 208 is placed across the operable face of the magnet array in the direction shown to provide SH-wave excitations. The direction of current flow in the SH-wave wire 208 is perpendicular to both the direction of the current in the Lamb wave wires (214 and 216) and to the magnetization direction of the static magnetic fields (204, 206).

The wavelength of the Lamb waves is determined by the distance between the Lamb wave generating wires. The wavelength of the SH waves is determined by the spatial period of the alternate pole magnet structure in X-direction. The length of the Lamb and the SH waves are shown in FIG. 9A at 217A and 217B respectively.

Figure 10A:
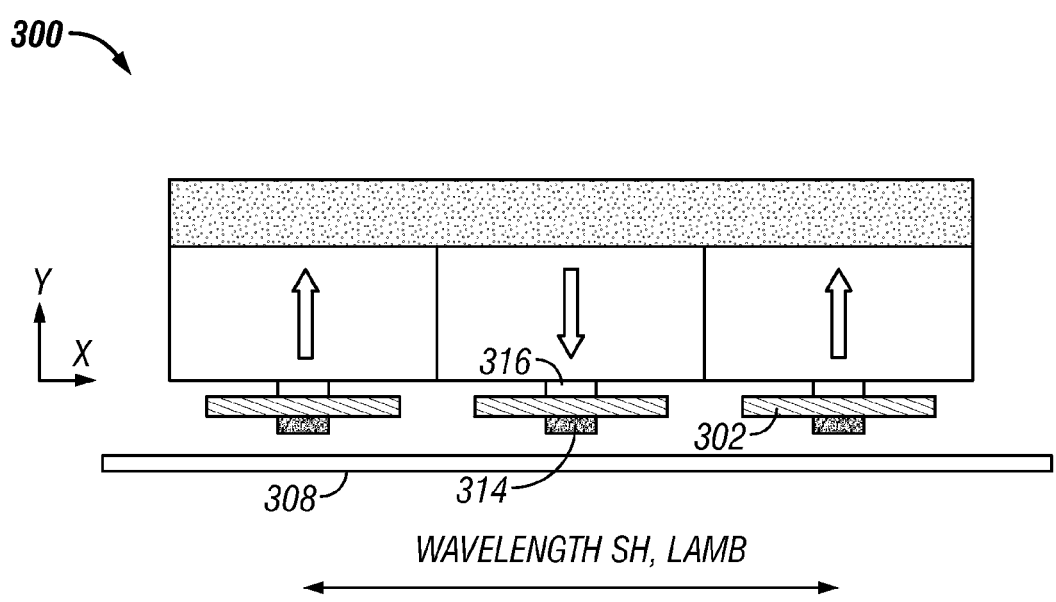
FIGS. 10A-B show an alternate embodiment of the EMAT of the present disclosure.
Figure 10B:
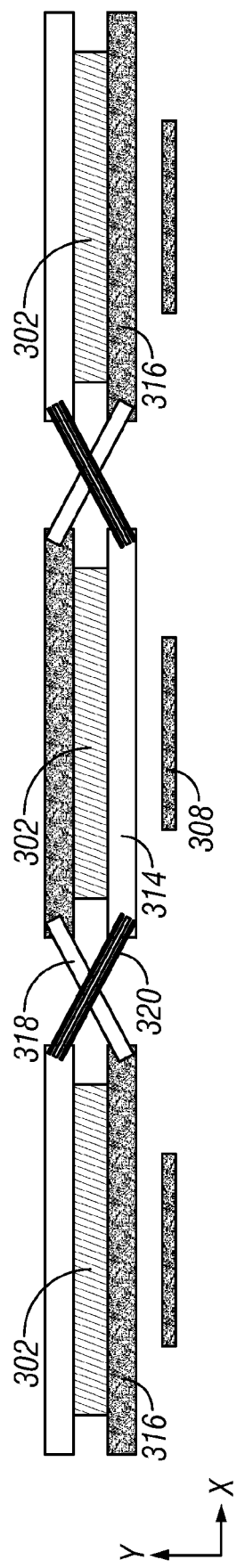

FIGS. 10A and 10B show an alternate embodiment of the EMAT of the present disclosure. A non-conductive soft magnetic material 302 is employed in order to increase the RF field generated by the excitation wires at the object surface per unit current in the wire as well as to simplify the return path of the Lamb-wave generating wire. The configuration of FIGS. 10A and 10B also produces SH and Lamb waves that have the same wavelength.

FIG. 10A shows a first side view of the alternate embodiment 300 of the EMAT using the non-conductive soft magnetic material. At the operable face of the magnetic array, Lamb wires 314 and 316 are oriented to carry current along a z-direction. The soft magnetic plate 302 is placed between wires 314 and 316. In the embodiment of the FIG. 10A, the Lamb wires are located between the SH-wave wire 308 and the magnet array.

FIG. 10B shows a second side view of the alternate embodiment. The wires 314 and 316 are seen to alternate between top and bottom faces of the soft magnetic material 302 using connectors 318 and 320. In such a configuration, the portion of Lamb current that is closest to the object of examination reverses direction between alternating magnetic regions, thereby achieving an effect comparable to that achieved using the exemplary embodiment of FIGS. 9A-B. The alternation of current directions at the face nearest the object of examination generally occurs at the interfaces between alternating magnets.

The invention has been described with reference to a device used with a conductive tubular in a borehole. This is not to be construed as a limitation of the invention; the method and apparatus described above may be used to generate shear waves and Lamb waves in a tubular or plate of any type of electrically conducting material. In such a case, the directions identified above would be referenced to a "first direction" instead of to "an axis of the tubular."

Implicit in the control and processing of the data is the use of a computer program on a suitable machine readable medium that enables the processor to perform the control and processing. The machine readable medium may include ROMs, EPROMs, EEPROMs, Flash Memories and Optical disks. Such a computer program may output the results of the processing to a suitable tangible medium. This may include a display device and/or a memory device.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. An apparatus configured for use with an electrically conducting material, the tool comprising:

(a) a magnet assembly including a plurality of magnets with alternating polarization in a direction substantially orthogonal to a first direction of a body of the electrically conducting material;

(b) a first conductor configured to carry a first current in a direction substantially parallel to the first direction and generate a shear wave in the body upon passage of the first current;

(c) a second conductor configured to carry a second current in a direction substantially orthogonal to the first direction and substantially orthogonal to the direction of polarization of the plurality of magnets and generate a Lamb wave upon passage of the second current;

(d) a receiving transducer configured to produce signals responsive to the generated shear wave and the generated Lamb wave; and (e) a processor configured to:
(I) use the produced signals to estimate a property of the received shear wave and the received Lamb wave, and
(II) record the estimated property on a suitable medium.

2. The apparatus of claim 1 wherein the electrically conducting material comprises a tubular conveyed in a borehole and the first direction comprises an axis of the tubular.

3. The apparatus of claim 1, wherein the plurality of magnets in the magnet assembly are arranged so that the alternating polarizations form a checkerboard pattern.

4. The apparatus of claim 1, wherein the first conductor is further configured to provide rows of the first current alternately carried in opposing directions along the magnet assembly.

5. The apparatus of claim 1, wherein the second conductor comprises at least one cross-over portion configured to maintain the generated Lamb wave in two adjacent regions of opposing magnet polarization.

6. The apparatus of claim 4, wherein the cross-over portion is configured to switch positions of a pair of wires which are placed one of i) side by side and equally separated from the magnet assembly, and, ii) on opposing sides of a non-conductive soft magnetic material and differently separated from the magnet assembly.

7. The apparatus of claim 1 wherein the first and second conductors are configured to be implemented as a multi-layer printed circuit board.

8. The apparatus of claim 1 wherein the property is selected from the group consisting of: (i) velocity, and (ii) attenuation.

9. The apparatus of claim 1, wherein the receiving transducer further comprises:
(a) a magnet assembly including a plurality of magnets with alternating polarization in a direction substantially orthogonal to the first direction;
(b) a first conductor configured to generate a first current in response to a received shear wave; and
(c) a second conductor configured to generate a second current in response to a received Lamb wave.

10. A method of generating acoustic waves in an electrically conducting material, the method comprising:
(a) providing a magnet assembly including a plurality of magnets with alternating polarization in a direction substantially orthogonal to a first direction of a body of the electrically conducting material;
(b) conveying a first current in a direction substantially parallel to the first direction to generate a shear wave in the electrically conducting material;
(c) conveying a second current in a direction substantially orthogonal to the first direction and substantially orthogonal to the direction of polarization of the plurality of magnets to generate a Lamb wave;
(d) producing signals responsive to the generated shear wave and the generated Lamb wave at a receiving transducer;
(e) estimating a property of the received shear wave and the received Lamb wave from the produced signals, and
(f) recording the estimate property on a suitable medium.

11. The method of claim 10 wherein the electrically conducting material comprises a tubular conveyed in a borehole and wherein the first direction comprises an axis of the tubular.

12. The method of claim 10, wherein providing the magnet assembly further comprises arranging the plurality of magnets so that the alternating polarizations form a checkerboard pattern.

13. The method of claim 10, wherein conveying the first current further comprises conveying the current in opposite directions.

14. The method of claim 10, wherein conveying the second current further comprises using a conductor having a cross-over portion.

15. The method of claim 14 wherein the cross-over portion maintains the generated Lamb wave in two adjacent regions of opposing magnet polarization.

16. The method of claim 14 wherein the cross-over portion switches the positions of a pair of wires which are placed one of i) side-by-side and equally separated from the magnet assembly, and, ii) on opposing sides of a non-conductive soft magnetic material and differently separated from the magnet assembly.

17. The method of claim 10 wherein the property is one of: velocity and attenuation.

18. The method of claim 10 wherein producing signals responsive to the shear wave and the Lamb wave further comprises:
(a) providing a magnet assembly including a plurality of magnets with alternating polarization in a direction substantially orthogonal to the first direction;
(b) generating a first current in a first conductor in response to the received shear wave; and
(c) generating a second current in a second conductor in response to the received Lamb wave.

19. A computer-readable medium for use with a tool for evaluating an electrically conducting material, the tool comprising:
(a) a magnet assembly including a plurality of magnets with alternating polarization in a direction substantially orthogonal to a first direction of a body of the electrically conducting material;
(b) a first conductor configured to carry a first current in a direction substantially parallel to the first direction and generate a shear wave in the body upon passage of the first current;
(c) a second conductor configured to carry a second current in a direction substantially orthogonal to the first direction and substantially orthogonal to the direction of polarization of the plurality of magnets and generate a Lamb wave upon passage of the second current; and
(d) a receiving transducer configured to produce signals responsive to the generated shear wave and the generated Lamb wave;
the medium comprising instructions which enable a processor to:
(e) estimate a velocity of the generated shear wave and the generated Lamb wave from the produced signals; and
(f) record the estimated velocities on a suitable medium.

20. The medium of claim 19 further comprising at least one of (i) a ROM, (ii) and EPROM, (iii) an EEPROM, (iv) a flash memory, and (v) an optical disk.

* * * * *